United States Patent
Hayakawa et al.

(10) Patent No.: US 11,938,269 B2
(45) Date of Patent: Mar. 26, 2024

(54) PRESSURE CONTROLLER

(71) Applicant: Murata Manufacturing Co., Ltd., Kyoto (JP)

(72) Inventors: Koichi Hayakawa, Kyoto (JP); Reo Matsumura, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 1293 days.

(21) Appl. No.: 16/217,452

(22) Filed: Dec. 12, 2018

(65) Prior Publication Data
US 2019/0111224 A1    Apr. 18, 2019

Related U.S. Application Data (63) Continuation of application No. PCT/JP2017/023084, filed on Jun. 22, 2017.

(30) Foreign Application Priority Data

Jul. 7, 2016    (JP) .................. 2016-135231

(51) Int. Cl.
*A61M 16/04*    (2006.01)
*A61M 16/00*    (2006.01)

(52) U.S. Cl.
CPC ... *A61M 16/044* (2013.01); *A61M 2016/0027* (2013.01); *A61M 2205/18* (2013.01);
(Continued)

(58) Field of Classification Search
CPC ...... A61M 16/044; A61M 16/04–0465; A61M 25/1018; A61M 25/10181; A61M 25/10184–10186
See application file for complete search history.

(56) References Cited

U.S. PATENT DOCUMENTS 4,383,534 A * 5/1983 Peters ............... A61M 16/0447
128/207.15
4,872,483 A * 10/1989 Shah ................... A61M 16/044
137/557
(Continued)

FOREIGN PATENT DOCUMENTS

JP    H07-163531 A    6/1995
JP    2009-103111 A    5/2009
(Continued)

OTHER PUBLICATIONS

International Search Report for International Application No. PCT/JP2017/023084, dated Sep. 19, 2017.
(Continued)

*Primary Examiner* — Joseph D. Boecker
*Assistant Examiner* — Thomas W Greig
(74) *Attorney, Agent, or Firm* — Pearne & Gordon LLP (57) ABSTRACT

A pressure controller 1 supplies fluid to a cuff and controls an internal pressure of the cuff. The pressure controller 1 has a housing 10 having a flattened shape. In the housing 10, a pump 31 having a discharge port 33 through which the fluid is discharged and which is directed in a thickness direction of the housing 10, and a control module 20 which controls the pump 31 such that the internal pressure of the cuff falls within a predetermined range, are disposed. A filter 39 which has elasticity and has lower thermal conductivity than the housing 10 is disposed at a side opposite to the discharge port 33 and between the pump 31 and an inner surface of the housing 10.

19 Claims, 8 Drawing Sheets

(52) U.S. Cl.
CPC .............. *A61M 2205/502* (2013.01); *A61M 2205/7545* (2013.01); *A61M 2205/8206* (2013.01)

(56) References Cited

U.S. PATENT DOCUMENTS

| | | | |
|---|---|---|---|
| 6,647,984 B1* | 11/2003 | O'Dea | A61M 16/044 128/207.15 |
| 2005/0159702 A1* | 7/2005 | Sekiguchi | A61B 1/00082 604/99.01 |
| 2008/0302363 A1* | 12/2008 | Kroupa | A61M 16/202 128/204.21 |
| 2012/0226172 A1 | 9/2012 | Doi et al. | |
| 2014/0366874 A1* | 12/2014 | Deutsch | A61B 5/7278 128/202.13 |
| 2016/0038699 A1* | 2/2016 | Higashiyama | A61M 16/0003 128/207.15 |
| 2018/0126105 A1* | 5/2018 | Pesenti | A61M 16/0445 |
| 2018/0333551 A1* | 11/2018 | Guo | A61B 5/091 |

FOREIGN PATENT DOCUMENTS

| | | |
|---|---|---|
| JP | 2009103111 A * | 5/2009 |
| JP | 2011-103983 A | 6/2011 |
| JP | 2012-217684 A | 11/2012 |
| WO | 2014/174957 A1 | 10/2014 |

OTHER PUBLICATIONS

Written Opinion for International Application No. PCT/JP2017/023084, dated Sep. 19, 2017.

* cited by examiner

PRESSURE CONTROLLER

This is a continuation of International Application No. PCT/JP2017/023084 filed on Jun. 22, 2017 which claims priority from Japanese Patent Application No. 2016-135231 filed on Jul. 7, 2016. The contents of these applications are incorporated herein by reference in their entireties.

BACKGROUND OF THE DISCLOSURE

Field of the Disclosure

The present disclosure relates to a pressure controller that controls the internal pressure of a bag-like member such as a cuff.

Description of the Related Art

In the related art, tracheal intubation has been known in medical fields regarding artificial ventilators. In tracheal intubation, an operator such as a medical doctor inserts an intubation tube into the trachea of a subject (usually, a human body) through the oral cavity or nasal cavity to maintain the airway, and oxygen is sent to the lungs via the intubation tube. When a gap is created between the intubation tube and the inner wall of the trachea, secretions such as gastric juice and saliva flow into the trachea, and the subject may develop ventilator-associated pneumonia. In order to prevent such secretion inflow, a cuff is provided to the outer wall of the intubation tube. The cuff inflates upon supply of gas into the cuff. As the cuff inflates, the outer periphery of the cuff comes into contact with the inner wall of the trachea to close the trachea. In this manner, in the related art, the secretions are prevented from flowing into the trachea with the cuff while the airway is maintained with the intubation tube.

The following problem has been known to arise when the level of the internal pressure of the cuff (hereinafter, referred to as "cuff pressure") falls out of a predetermined range. For example, when the cuff pressure exceeds the predetermined range, the inflated cuff compresses the blood vessels of mucosal tissues of the trachea. When the blood vessels are compressed, the blood vessels become ischemic. As a result, necrosis, bleeding, or the like may be caused. On the other hand, when the cuff pressure falls below the predetermined range, the inflation of the cuff becomes insufficient. This may create a gap between the outer periphery of the cuff and the inner wall of the trachea, and secretions such as gastric fluid and saliva may flow into the trachea. To address this problem, a cuff pressure control device that controls the cuff pressure within a predetermined range has been proposed (see, for example, Patent Document 1).

Patent Document 1: International Publication No. 2014/174957

BRIEF SUMMARY OF THE DISCLOSURE

Meanwhile, safe handling by an operator is required for the cuff pressure control device described above, and thus it is necessary to make the surface temperature of the cuff pressure control device equal to or lower than a desired temperature. In addition, for the cuff pressure control device, reducing the thickness of a housing in response to a demand for size reduction has been considered. In the thinned housing, a pump needs to be fixed in a main surface direction. The pump is driven for supplying gas to the cuff, but serves as a heating element that generates heat due to the operation thereof. When the thickness of the housing is reduced, the distance between the housing and the pump, which is a heating element, is decreased, and thus heat is easily transmitted to the housing when the pump is fixed in the main surface direction. Accordingly, the surface temperature of the housing may exceed a predetermined temperature. Low-temperature burn due to the long-term contact with the device at such a temperature is a concern.

The present disclosure has been made to solve the above problem, and an object of the present disclosure is to provide a pressure controller that is able to make the heat of a pump less likely to be transmitted, thereby inhibiting a rise in a surface temperature thereof, while achieving a reduction in the thickness of a housing.

A pressure controller that solves the above problem is a pressure controller which is connected to a bag-like member, supplies fluid to the bag-like member, and controls an internal pressure of the bag-like member, the pressure controller including: a housing having a flattened shape; a pump disposed in the housing such that a discharge port through which the fluid is discharged is directed in a thickness direction of the housing; a control module disposed in the housing and controlling the pump such that the internal pressure falls within a predetermined range; and a low thermal conductivity member disposed at a side opposite to the discharge port and between the pump and an inner surface of the housing, having elasticity, and having permeability.

According to this configuration, the pump is disposed such that the discharge port of the pump is directed in the thickness direction of the housing formed in a flattened shape. In this case, the surface of the pump at the side opposite to the surface of the pump in which the discharge port is formed is close to the housing. The low thermal conductivity member having elasticity and having permeability is disposed between the pump and the housing. Because of the presence of the low thermal conductivity member, the heat generated by the pump is less likely to be transmitted to the housing. Therefore, in the thinned housing, it is possible to inhibit a rise in the surface temperature of the housing.

In the above pressure controller, preferably, the pump has a first main surface and a second main surface, the discharge port is formed in the first main surface, and the low thermal conductivity member is disposed between the second main surface of the pump and the housing.

According to this configuration, by using the pump having the first main surface and the second main surface, it is possible to make the housing thin. By the low thermal conductivity member disposed between the pump and the housing, the heat of the pump becomes less likely to be transmitted to the housing, and thus it is possible to inhibit a rise in the surface temperature of the housing.

In the above pressure controller, a suction port through which the fluid is sucked is preferably provided in the second main surface.

According to this configuration, the pump discharges the fluid that is sucked through the suction port provided in the second main surface, through the discharge port formed in the first main surface.

In the above pressure controller, the low thermal conductivity member is preferably a filter which allows the fluid to pass therethrough.

According to this configuration, by the low thermal conductivity member which is the filter, it is possible to remove dust and the like in the fluid that is to be sucked into the pump.

In the above pressure controller, preferably, the control module has a wiring board fixed to the housing, the pump is disposed between the wiring board and the housing such that the discharge port is directed toward the wiring board, and a tube connected to the discharge port of the pump is an L-shaped tube in which a part of a passage is bent and a wall portion forming the passage is thick.

According to this configuration, when the pump moves, the tube comes into contact with the wiring board as a result of the movement of the pump. At this time, the thick wall portion comes into contact with the wiring board, so that movement of the pump is restricted. Thus, it is possible to inhibit the displacement of the pump.

In the above pressure controller, in the tube connected to the discharge port, the thick portion preferably has a flat surface portion opposing to a main surface of the wiring board.

According to this configuration, when the pump moves, the tube comes into contact with the wiring board as a result of the movement of the pump. At this time, by the flat surface portion coming into contact with the wiring board, the tube is less likely to be displaced in a direction parallel to the main surface of the wiring board. Thus, it is possible to stabilize the attitude of the pump.

In the above pressure controller, the flat surface portion of the thick portion of the tube is preferably in contact with the main surface of the wiring board.

According to this configuration, by the flat surface portion which is in contact with the wiring board, the tube is less likely to be displaced in the direction parallel to the main surface of the wiring board. Thus, it is possible to stabilize the attitude of the pump.

In the above pressure controller, the control module preferably includes a pressure sensor which measures the internal pressure of the bag-like member.

According to this configuration, it is possible to control the internal pressure on the basis of a result of the measurement by the pressure sensor.

With the pressure controller of the present disclosure, it is possible to make the heat of the pump less likely to be transmitted to inhibit a rise in the surface temperature of the housing, while achieving the reduction in the thickness of the housing.

DETAILED DESCRIPTION OF THE DISCLOSURE

Hereinafter, an embodiment will be described with reference to the accompanying drawings.

The accompanying drawings may show the components in an enlarged manner for easy understanding. The dimensional ratio of the components may be different from the actual one, or one in another drawing. In addition, some members may be omitted for easy understanding.

First, an application example of a pressure controller of the present embodiment will be described.

Figure 8A:
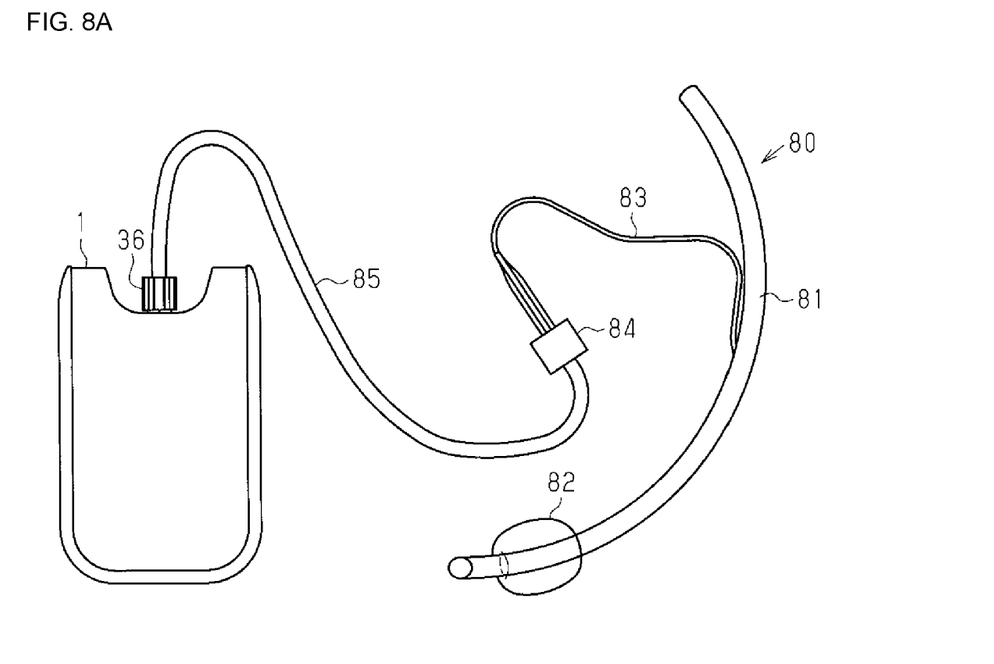
FIG. 8A is a schematic diagram showing the pressure controller and a cuff-equipped trachea tube.

As shown in FIG. 8A, a pressure controller 1 is connected to a cuff-equipped trachea tube 80 via a connection tube 85. The cuff-equipped trachea tube 80 has a trachea tube 81, a cuff 82, an inflation tube 83, and a lure connector 84.

The cuff 82 is provided at an end portion of the trachea tube 81 and at a predetermined position on the outer periphery of the trachea tube 81. A passage is formed within a wall portion of the trachea tube 81 so as to communicate with the interior of the cuff 82. One end of the inflation tube 83 is connected to the passage, and the other end of the inflation tube 83 is connected to the lure connector 84. One end of the connection tube 85 is connected to the lure connector 84, and the other end of the connection tube 85 is connected to the pressure controller 1. As the material of the trachea tube 81, the cuff 82, the connection tube 85, and the inflation tube 83, for example, polyvinyl chloride and an olefin-based elastomer may be used.

The pressure controller 1 controls the internal pressure (cuff pressure) of the cuff 82 connected thereto via the connection tube 85, the inflation tube 83, and the passage of the trachea tube 81. A check valve is provided in the lure connector 84 such that air in the cuff 82 is prevented from coming out even when the connection tube 85 is pulled out from the lure connector 84. Thus, when the pressure controller 1 is not used, it is possible to separate the pressure controller 1 and the connection tube 85, and the cuff-equipped trachea tube 80 from each other with the cuff pressure maintained, for example, by pulling out the connection tube 85 from the lure connector 84 in a state where the pressure controller 1 has controlled the cuff pressure.

Figure 8B:
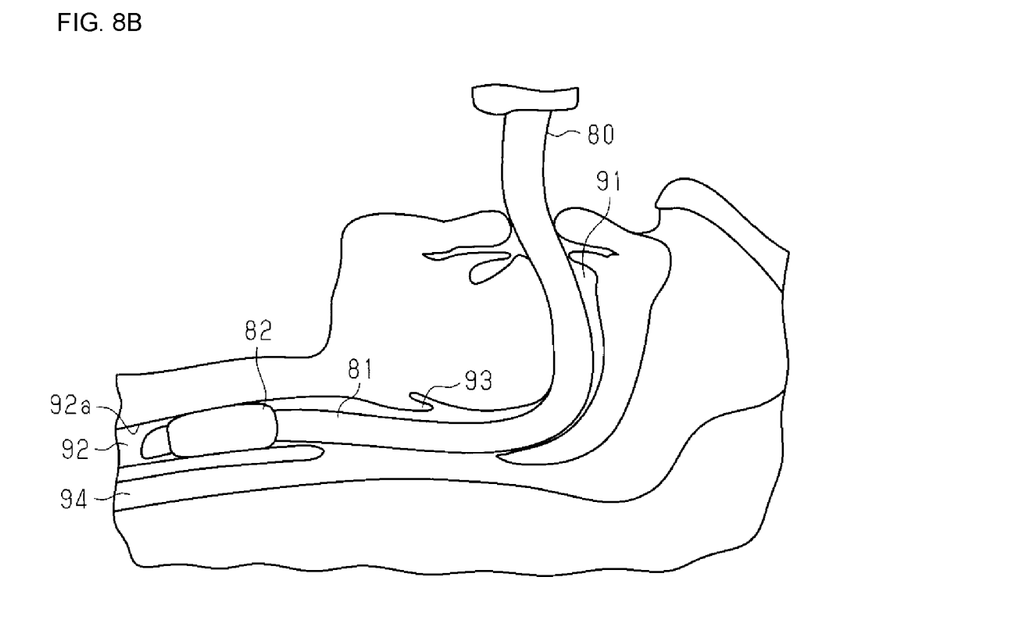
FIG. 8B is a schematic diagram showing a state where the trachea tube is used.

As shown in FIG. 8B, the trachea tube 81 is inserted through the oral cavity 91 of a subject into the trachea 92 of the subject. Accordingly, when an artificial ventilator is used, the airway is maintained by tracheal intubation. At this time, the epiglottis 93 becomes constantly opened, and thus secretions such as saliva may flow into the trachea 92 through a gap between the inserted trachea tube 81 and the inner wall 92a of the trachea 92. Reference sign 94 shown in FIG. 8B denotes esophagus.

In order to prevent such secretion inflow, the cuff 82, which is provided to the trachea tube 81, is inflated with the air supplied from the pressure controller 1 shown in FIG. 8A. The inflated cuff 82 comes into contact with the inner wall 92a of the trachea 92 to close the gap between the trachea tube 81 and the inner wall 92a of the trachea 92. By using such a cuff-equipped trachea tube 80, the cuff 82 is able to prevent secretions, etc. from flowing from the trachea 92 into the lungs, while the airway is maintained with the trachea tube 81.

The internal pressure (cuff pressure) of the cuff 82 needs to be appropriately maintained. If the cuff pressure is low, a gap may be created between the trachea tube 81 and the inner wall 92a of the trachea 92. On the other hand, if the cuff pressure is excessively high, the blood flow in the mucosae in the airway may be blocked and the mucosae may be damaged. The pressure controller 1 shown in FIG. 8A controls the cuff pressure such that the cuff pressure is equal to or higher than 20 cm $H_2O$ and equal to or lower than 30 cm $H_2O$, for example.

Next, the configuration of the pressure controller 1 will be described.

Figure 1A:
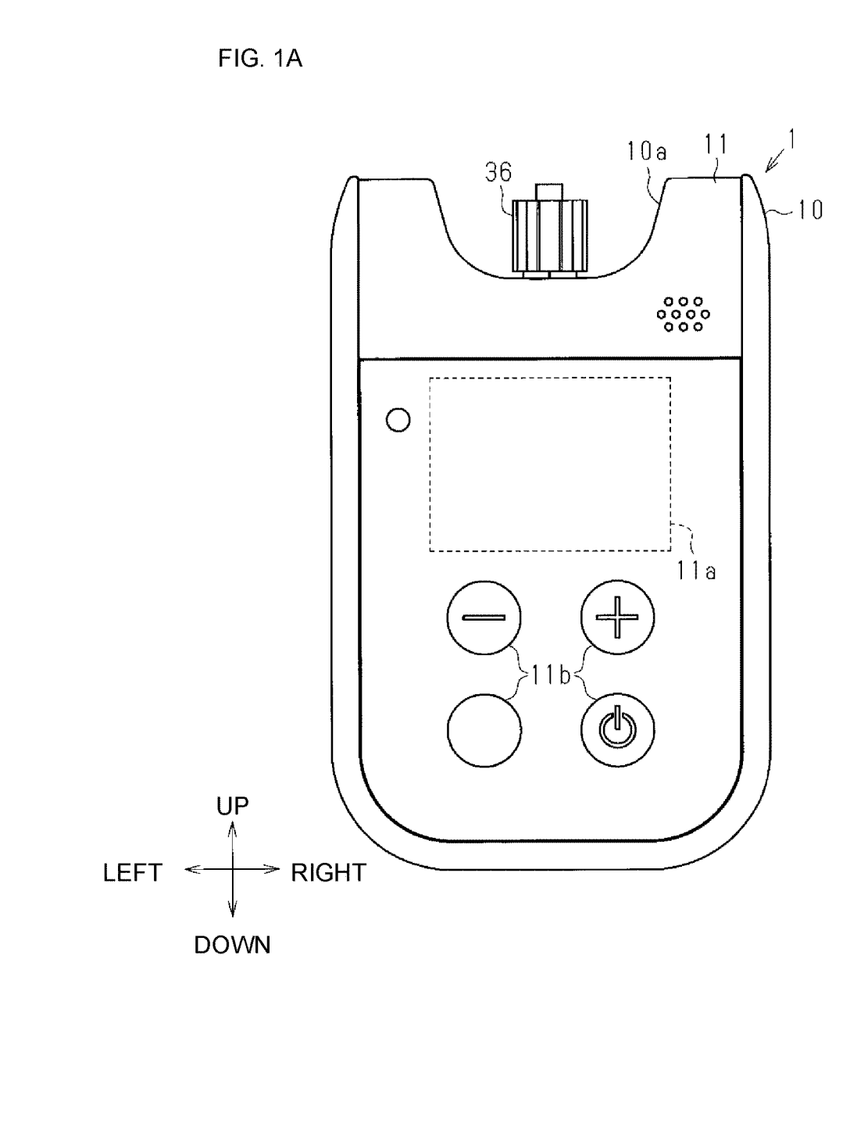
FIG. 1A is a front view of a pressure controller.
Figure 1B:
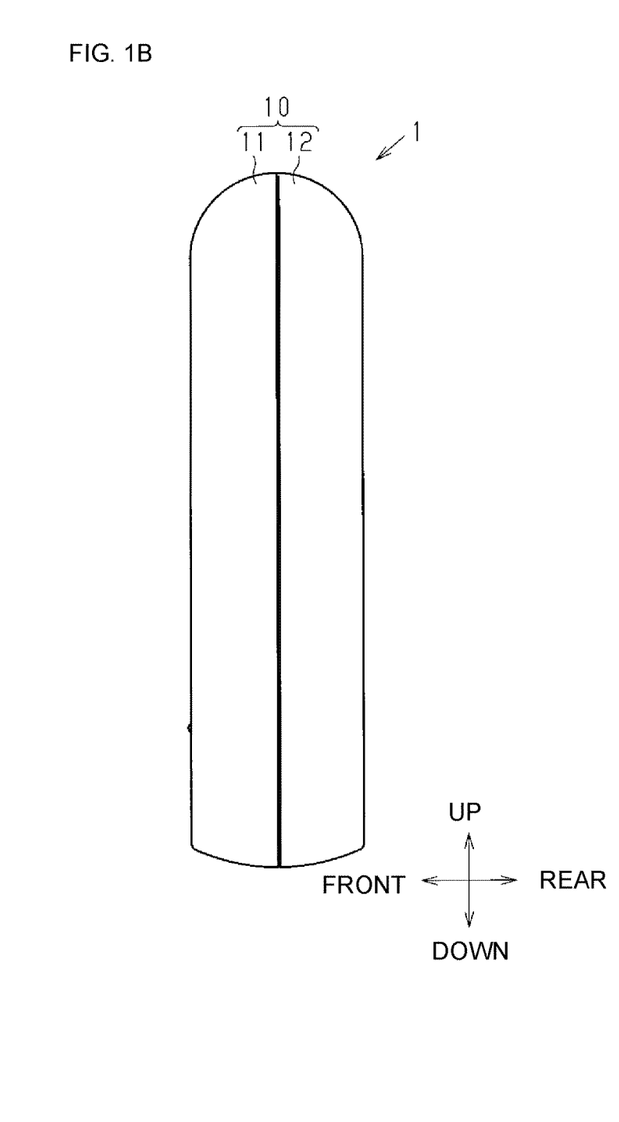
FIG. 1B is a side view of the pressure controller.

As shown in FIG. 1A and FIG. 1B, the pressure controller 1 is formed in a substantially flattened rectangular shape. In the following, a description will be sometimes given using the directions of the arrows shown in FIG. 1A and FIG. 1B.

As shown in FIG. 1B, a housing 10 has a front case 11 and a rear case 12. The front case 11 and the rear case 12 are connected to each other by means of fixing screws that are not shown. In the front case 11, a display portion 11a and a plurality of operation portions 11b are formed. The display portion 11a is formed such that a display panel 23 (see FIG. 2) disposed within the housing 10 is viewable from the outside of the housing 10 by an operator. The plurality of operation portions 11b indicate the positions of the operations switches disposed within the housing 10. For example, when the operator presses the operation portion 11b, the operation switch provided in corresponding relation to the operation portion 11b is turned on.

In FIG. 1A, an arc-shaped recess 10a is formed in an upper portion of the housing 10, and a lure connector 36 is disposed at the recess 10a. The connection tube 85 shown in FIG. 8A is connected to the lure connector 36.

Figure 2:
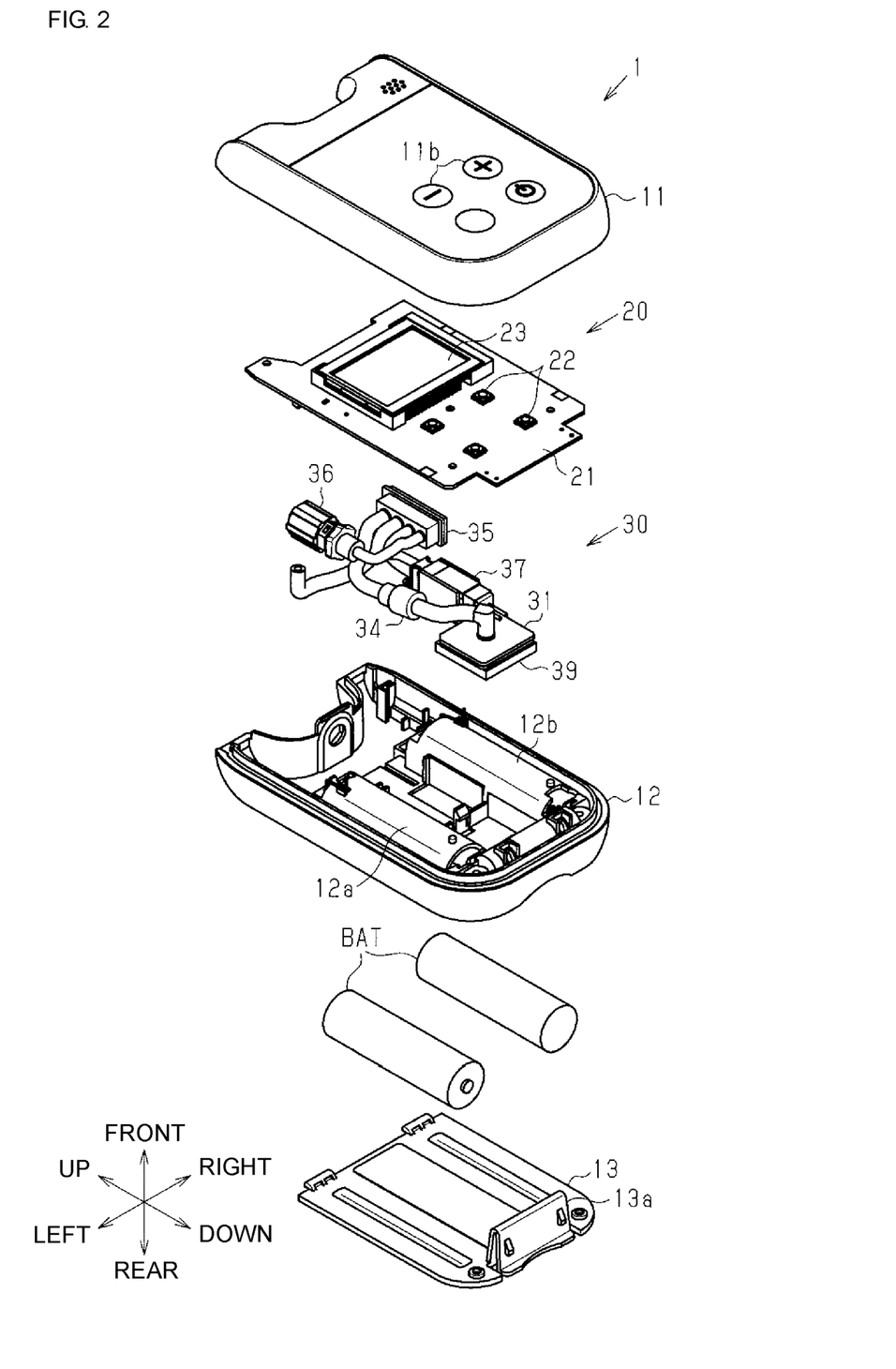
FIG. 2 is an exploded perspective view of the pressure controller.

As shown in FIG. 2, the pressure controller 1 has the front case 11, a control module 20, a fluid supply unit 30, the rear case 12, batteries BAT as a drive source, and a battery cover 13. The fluid supply unit 30 includes a pump 31, a check valve 34, a branch member 35, the lure connector 36, and a discharge valve 37. In FIG. 2, reference sings for the tubes connecting the pump 31, etc. are omitted. The front case 11 and the rear case 12 are formed so as to accommodate the control module 20 and the fluid supply unit 30. In the rear case 12, battery boxes 12a and 12b for accommodating the batteries BAT are integrally formed. The battery boxes 12a and 12b are closed by the battery cover 13 attached to the rear case 12.

In other words, the rear case 12 is partially covered with the battery cover 13. In the case of the pressure controller 1 of the present embodiment which operates by the batteries BAT as described above, the housing 10 includes the front case 11, the rear case 12, and the battery cover 13. In the present embodiment, the surface of the housing 10 includes the outer surface of the front case 11, the outer surface of the battery cover 13, the outer surface of a portion of the rear case 12 that is not covered with the battery cover 13.

In the case of a pressure controller that does not use the batteries BAT as a drive source, no battery cover is provided, and thus the surface of the housing includes the outer surface of a front cover and the entire outer surface of a rear cover. In addition, similarly, a pressure controller in which the batteries BAT are disposed inside a rear cover does not require a battery cover, and thus the surface of the housing includes the outer surface of a front cover and the entire outer surface of a rear cover.

Figure 4:
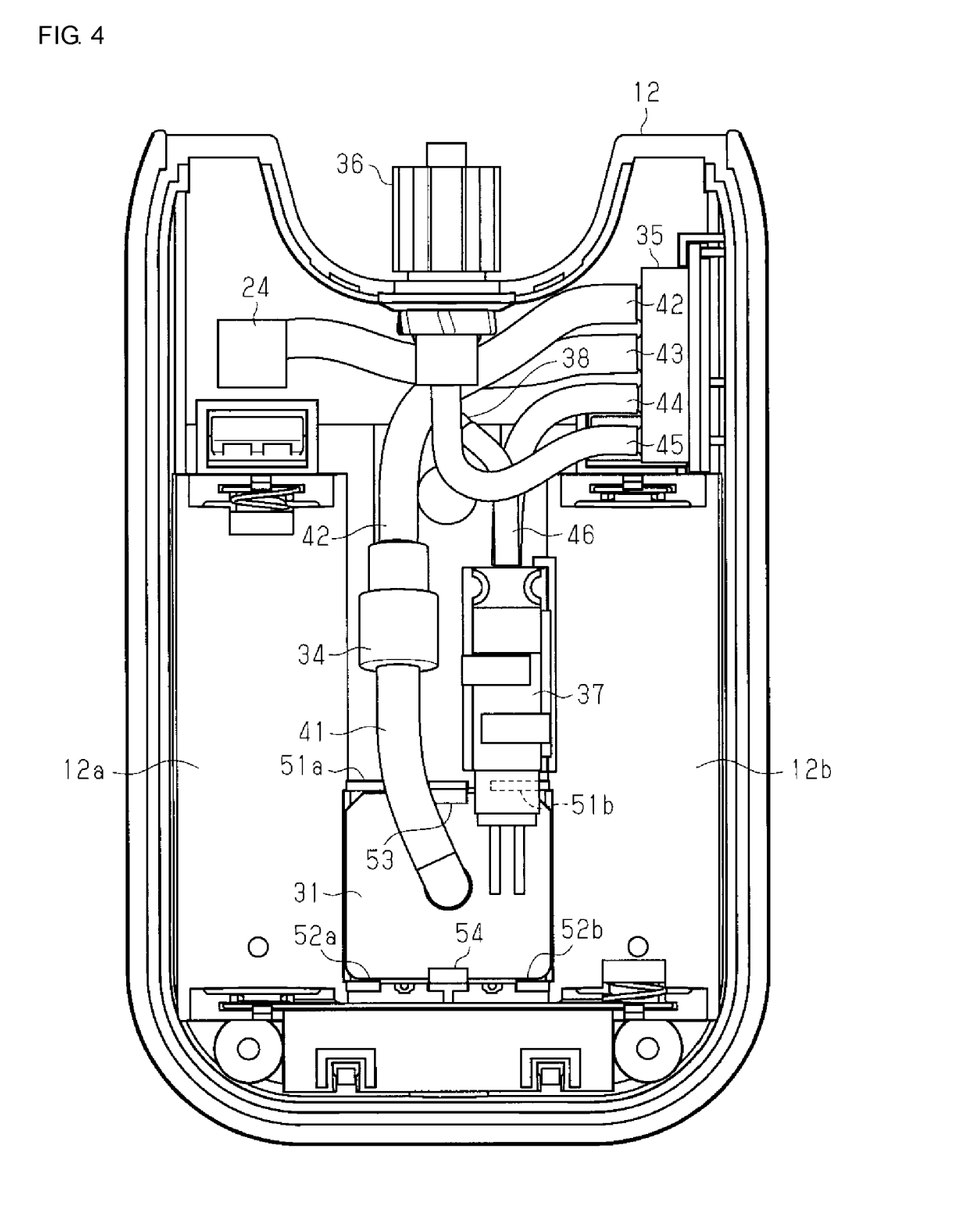
FIG. 4 is a plan view showing the interior of the pressure controller.

The battery boxes 12a and 12b are formed at both side portions of the rear case 12 (at the left and right sides in FIG. 4). The batteries BAT shown in FIG. 2 are accommodated into the battery boxes 12a and 12b from the outside of the rear case 12 (the back side in FIG. 4). The battery boxes 12a and 12b are closed by the battery cover 13 shown in FIG. 2. In this manner, the heavy batteries BAT are disposed at the left and right sides of the housing 10 (rear case 12). Thus, weight balance is better than in the case where batteries are accommodated in one end portion. Accordingly, it is possible to improve the holdability and the operability of the pressure controller 1.

The control module 20 includes a wiring board 21 and various electronic components. In FIG. 2, operation switches 22 and the display panel 23 are shown as electronic components mounted on the wiring board 21. On the wiring board 21, a pressure sensor 24, an integrated circuit device, a piezoelectric buzzer, etc., which are described later, are mounted as electronic components. The control module 20 is fixed to the rear case 12 by means of fixing screws that are not shown.

Next, the fluid supply unit 30 shown in FIG. 2 will be described.

Figure 5:
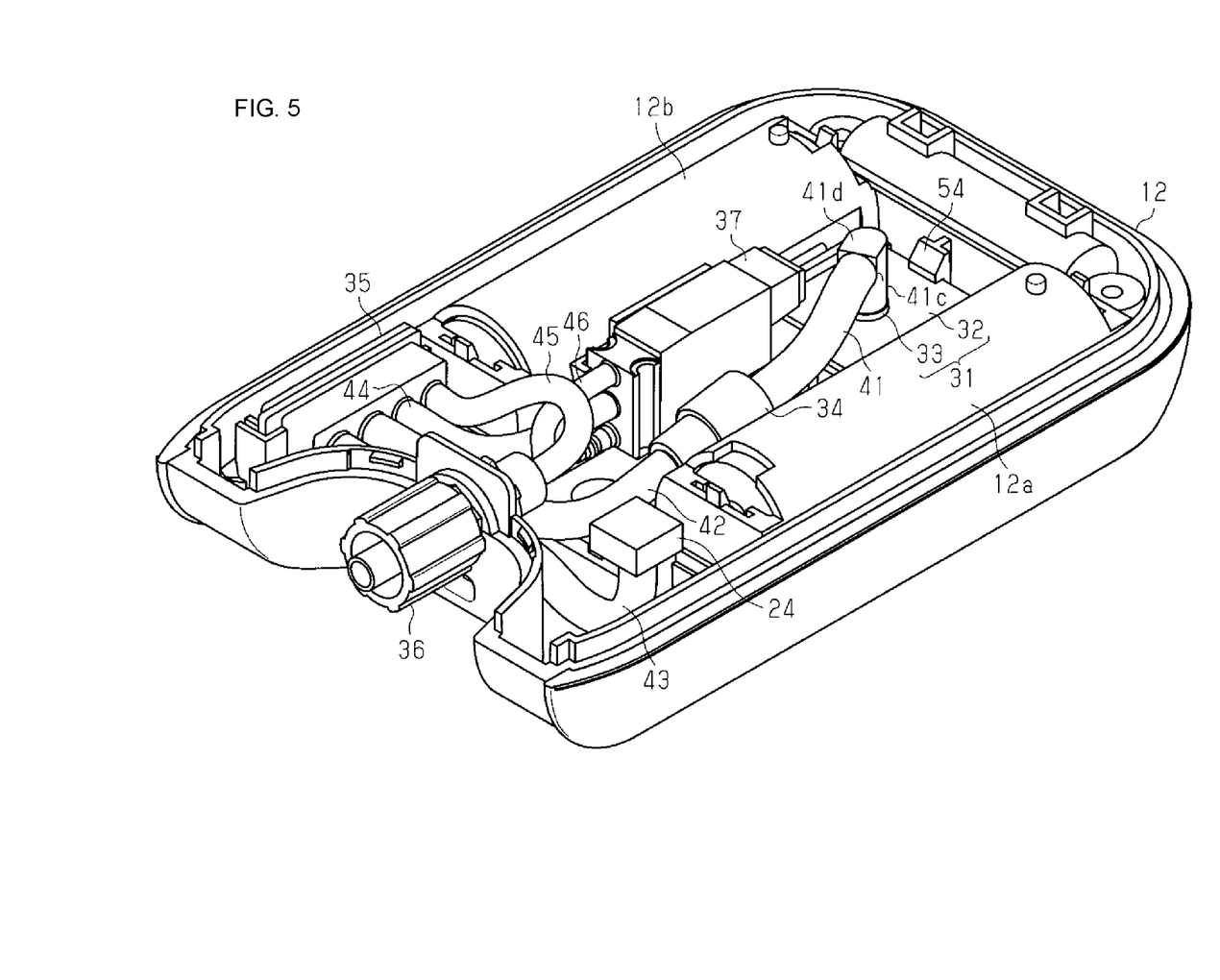
FIG. 5 is a perspective view showing the interior of the pressure controller.

As shown in FIG. 4 and FIG. 5, the fluid supply unit 30 includes the pump 31. The pump 31 is, for example, a piezoelectric pump, and has a pump body 32 formed in a flattened shape, and a discharge port 33 formed in one main surface 32a (the upper surface in FIG. 6) of the pump body 32. The piezoelectric pump is preferable as a pump for supplying fluid (gas) to the cuff 82, since fine adjustment of a supply amount of the fluid (gas) is easy.

The discharge port 33 of the pump 31 is connected to one end of the check valve 34 via a tube 41, and the other end of the check valve 34 is connected to the branch member 35 via a tube 42. The branch member 35 has four connection portions that communicate with each other, and the tubes 42, 43, 44, and 45 are connected thereto by the respective connection portions. The tube 45 is connected to the lure connector 36. The lure connector 36 is fixed to the rear case 12.

The pressure sensor 24 is connected to the tube 43. The pressure sensor 24 is mounted on the wiring board 21 shown in FIG. 2.

The tube 44 is connected to the discharge valve 37. As the discharge valve 37, for example, an electromagnetic valve (solenoid valve) may be used. One end of a tube 46 is connected to the discharge valve 37, and a capillary 38 is connected to the other end of the tube 46. The tube 44 and the tube 46 communicate with each other through the control of the discharge valve 37. Accordingly, air is discharged from the cuff 82 shown in FIG. 8A, so that the cuff pressure drops. The capillary 38 has a small hole having a smaller inner diameter than the passage of the tube 46 connected to the discharge valve 37. The capillary 38 limits a discharge flow rate and inhibits a rapid drop of the cuff pressure.

Figure 7:
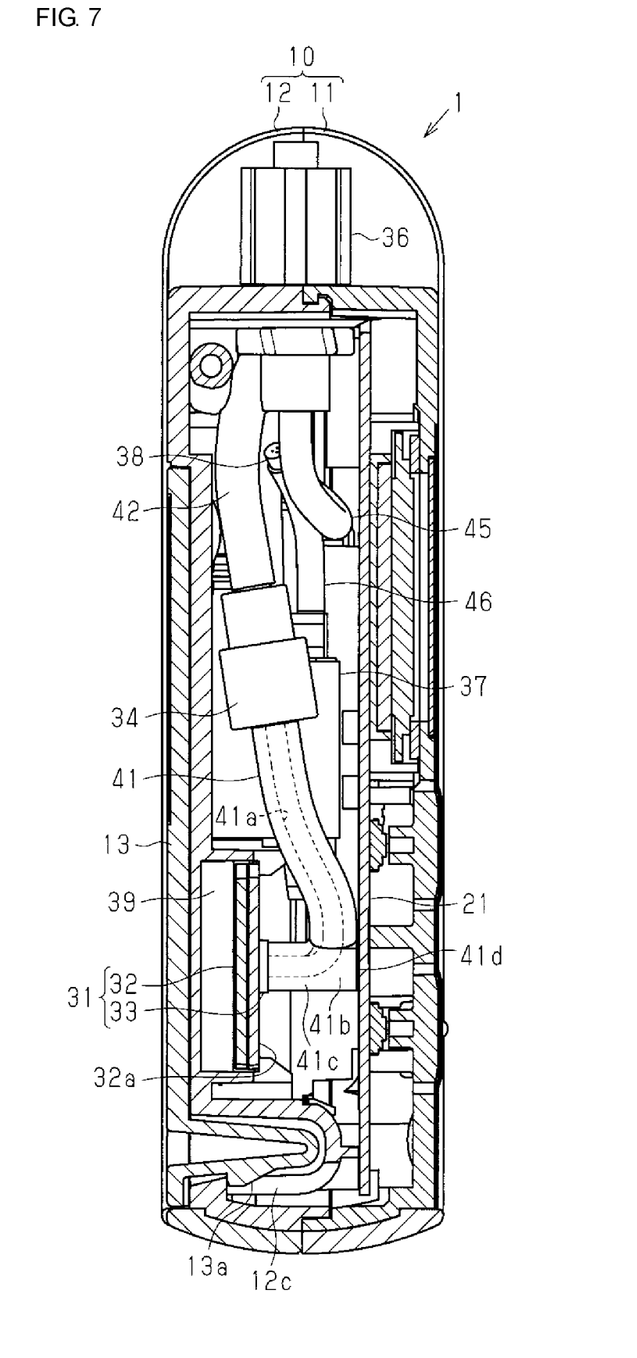
FIG. 7 is a lateral cross-sectional view of the pressure controller.

As shown in FIG. 7, the tube 41 connected to the pump 31 has an L-shaped connection portion connected to the pump 31. Specifically, a passage 41a through which the fluid discharged from the pump 31 passes is formed in the tube 41. The fluid flows from the pump 31 through the passage 41a to the check valve 34. The tube 41 has a thick wall portion 41b that is a part forming the passage 41a. The passage 41a is held in a bent state in an arc shape by the wall portion 41b. The tube 41 is formed in an L shape by the thick wall portion.

Figure 6:
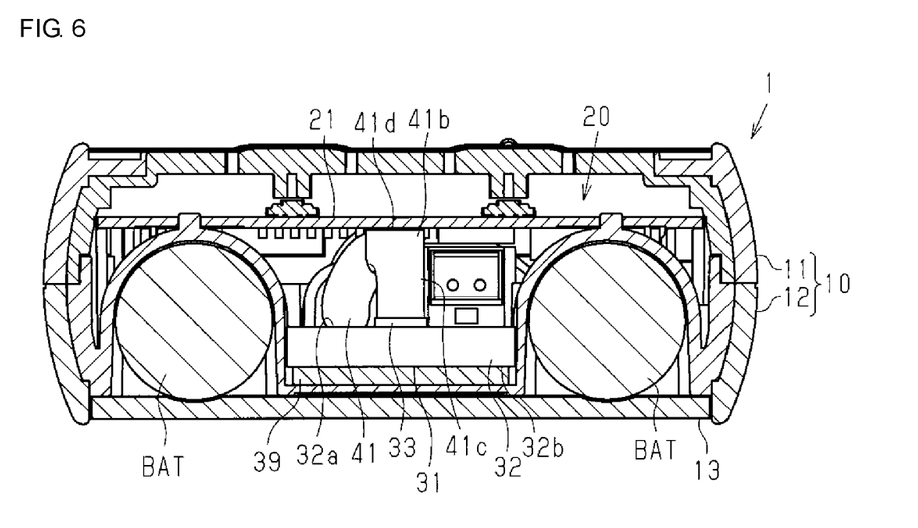
FIG. 6 is a longitudinal cross-sectional view of the pressure controller.

Because of the thick wall portion 41b, the tube 41 has a connection portion 41c extending in a direction perpendicular to the main surface 32a of the pump 31 (pump body 32). As shown in FIG. 5, the connection portion 41c has a proximal end at the pump 31 side and has a flat surface portion 41d formed at a distal end portion thereof. That is, the thick wall portion 41b has the flat surface portion 41d. The flat surface portion 41d opposes to the main surface of the wiring board 21 included in the control module 20. In the example of FIGS. 6 and 7, the flat surface portion 41d directly opposes to the wiring board 21 or is in contact with the wiring board 21. The connection portion 41c is able to serve as a spacer that forms an air gap between the wiring board 21 and the pump 31 and maintains the wiring board 21 and the pump 31 such that the wiring board 21 and the pump 31 are not in contact with each other.

As shown in FIG. 7, an engagement portion 12c is formed at a lower portion of the rear case 12. An elastic engagement piece 13a of the battery cover 13 attached to the rear case 12 is inserted into the engagement portion 12c. The elastic engagement piece 13a inserted into the engagement portion 12c is engaged with the rear case 12, and the battery cover 13 is fixed to the rear case 12 because of the engagement.

As shown in FIG. 6, a filter 39 and the pump 31 are disposed at the center in the right-left direction of the rear case 12 (the center in the right-left direction in the drawing). In the rear case 12, the filter 39 and the pump 31 are disposed in this order from the rear case 12 toward the front case 11. That is, the filter 39 is disposed between the pump 31 and the rear case 12. The battery cover 13 is attached to the rear case 12.

In the present embodiment, the pump 31 has a suction portion formed in a surface (the lower surface in FIG. 6) of the pump body 32 at the side opposite to the surface (the upper surface in FIG. 6) of the pump body 32 in which the discharge port 33 is formed. The pump 31 has, for example, three suction ports, and each suction port has a diameter of, for example, 0.3 to 0.5 mm.

The filter 39 is formed in a thin plate shape having a flat surface shape that is substantially the same as the flat surface shape of the pump 31. The filter 39 is made of, for example, a resin and has elasticity. The filter 39, which is disposed between the pump 31 and the rear case 12, elastically supports the pump 31. In addition, the filter 39 has, for example, lower thermal conductivity than the rear case 12. That is, the filter 39 is a low thermal conductivity member having lower thermal conductivity than the rear case 12.

As shown in FIG. 4, the pump 31, which is accommodated in the rear case 12, is formed in a substantially quadrangular shape in a plan view (as seen in the front surface in FIG. 4). The rear case 12 has restriction walls 51a and 51b which are disposed above the pump 31 (at an upper portion in the drawing), and restriction walls 52a and 52b which are disposed below the pump 31 (at a lower portion in the drawing). The respective restriction walls 51a, 51b, 52a, and 52b are formed so as to extend in the right-left direction of the rear case 12 (in the right-left direction in the drawing). These restriction walls 51a, 51b, 52a, and 52b, together with the battery boxes 12a and 12b, form an accommodation portion in which the pump 31 is accommodated. Movement of the pump 31 in the up-down direction of the rear case 12 is restricted by the restriction walls 51a, 51b, 52a, and 52b. In addition, movement of the pump 31 in the right-left direction of the rear case 12 is restricted by the battery boxes 12a and 12b.

Engagement pieces 53 and 54 are provided between the restriction walls 51a and 51b and between the restriction walls 52a and 52b, respectively, so as to be erected from the rear case 12. As shown in FIG. 7, the engagement pieces 53 and 54 are engaged with the main surface 32a of the pump (pump body 32) and restrict the movement of the pump 31 in the direction toward the upper surface (the upward direction in FIG. 6). The above-described filter 39 has elasticity (cushioning properties) and biases the pump 31 upward. That is, the filter 39 biases the pump 31 in the direction away from the rear case 12. The filter 39 has lower thermal conductivity than the rear case 12. Therefore, the heat generated from the pump 31 during driving is less likely to be transmitted to the rear case 12. The battery cover 13 is attached to the rear case 12. Thus, a rise in the surface temperature of the housing 10 (battery cover 13) is inhibited.

As shown in FIG. 4 and FIG. 5, the pump 31 is disposed between the battery boxes 12a and 12b, which are formed at the left and right sides of the rear case 12. Movement of the pump 31 in the right-left direction relative to the rear case 12 is restricted by the battery boxes 12a and 12b.

Figure 3:
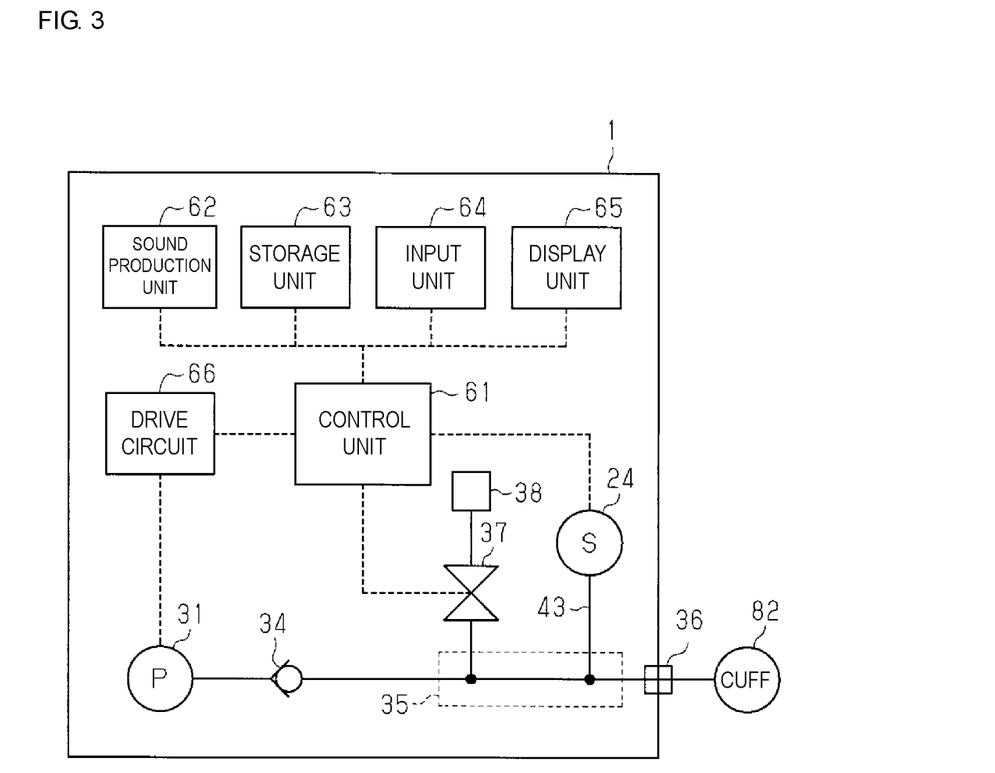
FIG. 3 is a block diagram functionally showing the pressure controller.

FIG. 3 is a block diagram functionally showing the pressure controller 1 of the present embodiment. The pump 31 of the pressure controller 1 is connected to the lure connector 36 via a connection path (tube) shown by a solid line in the drawing. The cuff 82 is connected to the lure connector 36. The pressure controller 1 controls the internal pressure (cuff pressure) of the cuff 82 to an appropriate value as described above.

The pressure controller 1 has a control unit 61, a sound production unit 62, a storage unit 63, an input unit 64, a display unit 65, a drive circuit 66, the pressure sensor (shown as "S" in the drawing) 24, the discharge valve 37, a pump (shown as "P" in the drawing), the check valve 34, and the branch member 35. The control unit 61, the storage unit 63, the display unit 65, the sound production unit 62, the input unit 64, and the drive circuit 66 are mounted, for example, as one integrated circuit device (for example, a micro control unit: MCU) on the wiring board 21 of the control module 20 shown in FIG. 2. The pressure sensor 24 is mounted on the wiring board 21 shown in FIG. 2. The pump 31 is connected to the drive circuit 66, and the discharge valve 37 and the pressure sensor 24 are connected to the control unit 61.

For example, as shown in FIG. 2, the input unit 64 includes the operation switches 22 mounted on the wiring board 21. The control unit 61 registers a setting range for the cuff pressure in the storage unit 63 on the basis of an operation of the input unit 64. The display unit 65 includes the display panel 23 shown in FIG. 2. The control unit 61 displays a result of measurement of the cuff pressure, the setting range for the cuff pressure, etc. on the display unit 65. The sound production unit 62 is, for example, a piezoelectric buzzer (not shown) or the like mounted on the wiring board 21 shown in FIG. 2. The control unit 61 drives the sound production unit 62 to emit an operation sound for the input unit 64, or a warning about occurrence of a certain abnormality or the like.

The control unit 61 compares the setting range registered in the storage unit 63 to a value of the cuff pressure measured by the pressure sensor 24, and controls at least one of the pump 31 and the discharge valve 37 in accordance with the difference therebetween. The pressure sensor 24 measures the internal pressure of the tube 43, which is connected to the branch member 35. Since the tube 43 communicates with the cuff 82, the internal pressure of the tube 43 is equal to the internal pressure of the cuff 82. That is, the pressure sensor 24 indirectly measures the internal pressure (cuff pressure) of the cuff 82.

For example, when the value of the cuff pressure is lower than the setting range (the minimum value), the control unit 61 drives the pump 31 to supply fluid (air) to the cuff 82. At this time, the discharge valve 37 is closed. For example, a normally closed port (N.C.: normally closed) is used in the discharge valve 37. When the cuff pressure rises to a pressure within the setting range as a result of the driving of the pump 31, the control unit 61 stops the pump 31.

When the diameter of the trachea changes due to a change in the attitude of a subject (patient), the cuff pressure becomes higher than the setting range (the upper limit) in some cases. In such a case, the control unit 61 opens the discharge valve 37. Accordingly, air is discharged through the cuff 82, so that the cuff pressure drops. When the cuff pressure drops to a pressure within the setting range, the control unit 61 closes the discharge valve 37. In this manner, the control unit 61 controls the pump 31 and the discharge valve 37 such that the cuff pressure falls within the setting range.

Next, operation of the above pressure controller 1 will be described.

As shown in FIG. 7, the housing 10 is formed in a flattened shape. The pump 31 is disposed such that the discharge port 33 is directed in the thickness direction of the housing 10. In this case, a main surface 32*b* of the pump 31 at the side opposite to the discharge port 33 is close to the housing 10 (rear case 12). In the present embodiment, the filter 39, which serves as the low thermal conductivity member, is disposed between the rear case 12 and the main surface 32*b* of the pump 31 at the side opposite to the main surface 32*a* in which the discharge port 33 is formed. Thus, the heat generated by the pump 31, which is disposed close to the rear case 12, is less likely to be transmitted to the rear case 12 because of the presence of the filter 39. Thus, a rise in the surface temperature of the rear case 12 is inhibited.

The filter 39 has elasticity and supports the pump 31. Therefore, when impact is applied to the housing 10 due to fall or the like, force due to the impact is not directly applied to the pump 31, because of the presence of the filter 39. In addition, because of the cushioning property of the filter 39, the force due to the impact is reduced. Thus, it is possible to protect the pump 31.

As described above, the pump 31 is disposed such that the discharge port 33 is directed in the thickness direction of the housing 10. Therefore, the pump 31 is disposed so as to be spaced apart from the discharge port 33 side, that is, the front case 11 of the housing 10, because of the presence of the discharge port 33. In addition, in the present embodiment, the wiring board 21 of the control module 20 is disposed between the pump 31 and the front case 11. Thus, the heat generated by the pump 31 is less likely to be transmitted to the front case 11, so that a rise in the surface temperature of the front case 11 is inhibited.

As shown in FIG. 4, the pump 31 is disposed between the two battery boxes 12*a* and 12*b*, which are integrally formed in the rear case 12. Therefore, the heat generated by the pump 31 is less likely to be transmitted to the right and left side surfaces of the housing 10, so that a rise in the surface temperature of the housing 10 is inhibited.

As shown in FIG. 7, the tube 41, which is formed in an L shape, is connected to the discharge port 33 of the pump 31. In the tube 41, the wall portion 41*b*, which forms the inner passage 41*a*, is thick. Thus, for example, when the pump 31 moves toward the wiring board 21, the thick wall portion 41*b* comes into contact with the wiring board 21 to restrict the movement of the pump 31. Accordingly, it is possible to inhibit the displacement of the pump 31. In the present specification, the wording L shape refers to a tube shape in a mode in which, in a device in which a discharge port of a pump and a wiring board oppose to each other, a flat portion (for example, the flat surface portion 41*d*) is provided at an outer peripheral portion of a tube and is able to come into contact with the wiring board, and the tube communicates with the discharge port of the pump at an end portion thereof away from the flat portion (for example, the connection portion 41*c*). That is, the appearance of the tube does not necessarily have an L shape, and the tube only needs to have a flat portion with a partially bent shape.

The wall portion 41*b* has the flat surface portion 41*d* and the flat surface portion 41*d* opposes to the main surface of the wiring board 21. For example, when the pump 31 moves toward the wiring board 21 due to the impact or the like applied to the pressure controller 1, the flat surface portion 41*d* of the wall portion 41*b* comes into contact with the main surface of the wiring board 21. Accordingly, the wall portion 41*b* of the tube 41 is less likely to be displaced relative to the wiring board 21 in a direction parallel to the main surface of the wiring board 21, and thus it is possible to stabilize the attitude of the pump 31.

As described above, the present embodiment achieves the following advantageous effects.

(1) The pressure controller 1 is connected to the cuff 82, supplies the fluid to the cuff 82, and controls the internal pressure of the cuff 82. The pressure controller 1 has the housing 10 having a flattened shape. In the housing 10, the pump 31 in which the discharge port 33, through which the fluid is discharged, is directed in the thickness direction of the housing 10, and the control module 20 which measures the internal pressure of the cuff 82 and controls the pump 31 such that the internal pressure thereof falls within a predetermined range on the basis of a result of the measurement, are disposed. The filter 39, which has elasticity and has lower thermal conductivity than the housing 10, is disposed at the side opposite to the discharge port 33 and between the pump 31 and the inner surface of the housing 10.

In this case, the surface of the pump 31 at the side opposite to the surface of the pump 31 in which the discharge port 33 is formed is close to the housing 10. The filter 39, which has lower thermal conductivity than the housing 10, is disposed between the pump 31 and the housing 10. Because of the presence of the filter 39, the heat generated by the pump 31 is less likely to be transmitted to the housing 10. Therefore, in the thinned housing 10, it is possible to inhibit a rise in the surface temperature of the housing 10.

(2) The pump 31 has a flattened shape and has the discharge port 33 formed in the first main surface 32*a*, and the filter 39 is disposed between the second main surface 32*b* of the pump 31 and the housing 10. According to this configuration, by using the pump 31 having a flattened shape, it is possible to make the housing 10 thin. By the filter 39 disposed between the pump 31 having a flattened shape and the housing 10, the heat of the pump 31 becomes less likely to be transmitted to the housing 10, and thus it is possible to inhibit a rise in the surface temperature of the housing 10.

(3) The suction port, through which the fluid is sucked, is provided in the main surface 32*b* of the pump 31 (pump body 32). Therefore, by the filter 39, it is possible to remove the dust and the like of the fluid that is to be sucked into the pump 31.

(4) The control module 20 has the wiring board 21 which is fixed to the housing 10 and on which at least the pressure sensor 24, which measures the internal pressure of the cuff 82, is mounted. The pump 31 is disposed between the wiring board and the housing 10 such that the discharge port 33 is directed toward the wiring board 21. The tube 41, which is connected to the discharge port 33 of the pump 31, is an L-shaped tube in which a part of the passage 41*a* has an arc shape and the wall portion 41*b* forming the arc-shaped passage 41*a* is thick. For example, when the pump 31 moves, the tube 41 comes into contact with the wiring board 21 as a result of the movement of the pump 31. At this time, the thick wall portion 41*b* comes into contact with the wiring board 21, and the movement of the pump 31 is restricted. Thus, it is possible to inhibit the displacement of the pump 31.

(5) In the tube 41 connected to the discharge port 33 of the pump 31, the thick wall portion 41b has the flat surface portion 41d opposing to the main surface of the wiring board 21. For example, when the pump 31 moves, the tube 41 comes into contact with the wiring board 21 as a result of the movement of the pump 31. At this time, by the flat surface portion 41d coming into contact with the wiring board 21, the tube 41 is less likely to be displaced in the direction parallel to the main surface of the wiring board 21. Thus, it is possible to stabilize the attitude of the pump 31.

Each embodiment described above may be carried out in the following modes.

The pressure controller 1 of the above embodiment controls the internal pressure (cuff pressure) of the cuff 82, which is provided to the trachea tube 81. However, the object to be controlled only needs to be a bag-like member, and the pressure controller 1 may control, for example, the internal pressure of a balloon of a balloon catheter, or the like.

In the above embodiment, the batteries BAT are provided as the drive source. However, an external power supply such as an AC adapter may be connected as the drive source to the housing 10. In addition, the batteries BAT and the external power supply may be used in combination.

In the above embodiment, the check valve 34 is connected between the pump 31 and the branch member 35 as shown in FIG. 3, but a pump having the function of a check valve may be used and the check valve 34 may be omitted.

In the above embodiment, the pump 31 having the suction port in the main surface 32b at the side opposite to the main surface 32a in which the discharge port 33 is formed is used, but a pump having a suction port in a side surface thereof or in a surface thereof in which the discharge port 33 is formed may be used.

In the above embodiment, a member having elasticity (cushioning properties) may be inserted between the rear case 12 and a part or all of side surfaces of the pump 31 which are different from the main surfaces 32a and 32b. For example, a sponge may be used as the member that is to be inserted. By such a member, it is possible to inhibit the movement of the pump 31.

The tube 41 described in the above embodiment is an example, and the passage 41a may be bent in any shape such as at a right angle.

In the above embodiment, the cuff pressure is measured by the pressure sensor 24, but the cuff pressure may be obtained by another method, for example, on the basis of the current of the pump or the like.

In the tube 41 of the above embodiment, the flat surface portion 41d of the thick wall portion 41b may be brought into contact with the main surface of the wiring board 21.

1 pressure controller
10 housing
20 control module
31 pump
33 discharge port
39 filter
82 cuff

The invention claimed is:

1. A pressure controller connected to a bag-like member, supplying fluid to the bag-like member, and controlling an internal pressure of the bag-like member, the pressure controller comprising:
   a housing having a flattened shape with a first surface on which a display is installed and a second surface opposite to the first surface;
   a pump disposed in the housing such that a discharge port through which the fluid is discharged is directed in a thinnest thickness direction of the flattened shape of the housing;
   a control module disposed in the housing and controlling the pump such that the internal pressure falls within a predetermined range; and
   a low thermal conductivity member disposed at a side opposite to the discharge port and between the pump and the second surface of the housing, the low thermal conductivity member having elasticity and permeability.

2. The pressure controller according to claim 1, wherein
   the pump has a first main surface and a second main surface, and the discharge port is provided in the first main surface, and
   the low thermal conductivity member is disposed between the second main surface of the pump and the housing.

3. The pressure controller according to claim 2, wherein a suction port through which the fluid is sucked is provided in the second main surface of the pump.

4. The pressure controller according to claim 1, wherein the low thermal conductivity member is a filter allowing the fluid to pass through the filter.

5. The pressure controller according to claim 1, wherein
   the control module has a wiring board fixed to the housing,
   the pump is disposed between the wiring board and the housing such that the discharge port is directed toward the wiring board, and
   a tube connected to the discharge port of the pump is an L-shaped tube, wherein a part of a passage of the L-shaped tube is bent and a wall portion forming the passage is thicker than other portions of the L-shaped tube.

6. The pressure controller according to claim 5, wherein, in the tube connected to the discharge port, the thicker portion has a flat surface portion opposing to a main surface of the wiring board.

7. The pressure controller according to claim 6, wherein the flat surface portion of the thicker portion of the tube is in contact with the main surface of the wiring board.

8. The pressure controller according to claim 1, wherein the control module has a pressure sensor measuring the internal pressure of the bag-like member.

9. The pressure controller according to claim 2, wherein the low thermal conductivity member is a filter allowing the fluid to pass through the filter.

10. The pressure controller according to claim 3, wherein the low thermal conductivity member is a filter allowing the fluid to pass through the filter.

11. The pressure controller according to claim 2, wherein
    the control module has a wiring board fixed to the housing,
    the pump is disposed between the wiring board and the housing such that the discharge port is directed toward the wiring board, and
    a tube connected to the discharge port of the pump is an L-shaped tube, wherein a part of a passage of the L-shaped tube is bent and a wall portion forming the passage is thicker than other portions of the L-shaped tube.

12. The pressure controller according to claim 3, wherein the control module has a wiring board fixed to the housing, the pump is disposed between the wiring board and the housing such that the discharge port is directed toward the wiring board, and a tube connected to the discharge port of the pump is an L-shaped tube, wherein a part of a passage of the L-shaped tube is bent and a wall portion forming the passage is thicker than other portions of the L-shaped tube.

13. The pressure controller according to claim 4, wherein the control module has a wiring board fixed to the housing, the pump is disposed between the wiring board and the housing such that the discharge port is directed toward the wiring board, and a tube connected to the discharge port of the pump is an L-shaped tube, wherein a part of a passage of the L-shaped tube is bent and a wall portion forming the passage is thicker than other portions of the L-shaped tube.

14. The pressure controller according to claim 2, wherein the control module has a pressure sensor measuring the internal pressure of the bag-like member.

15. The pressure controller according to claim 3, wherein the control module has a pressure sensor measuring the internal pressure of the bag-like member.

16. The pressure controller according to claim 4, wherein the control module has a pressure sensor measuring the internal pressure of the bag-like member.

17. The pressure controller according to claim 5, wherein the control module has a pressure sensor measuring the internal pressure of the bag-like member.

18. The pressure controller according to claim 6, wherein the control module has a pressure sensor measuring the internal pressure of the bag-like member.

19. The pressure controller according to claim 7, wherein the control module has a pressure sensor measuring the internal pressure of the bag-like member.

* * * * *